(12) United States Patent
Esteller et al.

(10) Patent No.: US 10,926,092 B2
(45) Date of Patent: Feb. 23, 2021

(54) AUTOMATIC ADJUSTMENT OF SUB-PERCEPTION THERAPY IN AN IMPLANTABLE STIMULATOR USING DETECTED COMPOUND ACTION POTENTIALS

(71) Applicant: Boston Scientific Neuromodulation Corporation, Valencia, CA (US)

(72) Inventors: Rosana Esteller, Santa Clarita, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 150 days.

(21) Appl. No.: 16/238,151

(22) Filed: Jan. 2, 2019

(65) Prior Publication Data

US 2019/0209844 A1    Jul. 11, 2019

Related U.S. Application Data

(60) Provisional application No. 62/614,736, filed on Jan. 8, 2018.

(51) Int. Cl.
*A61N 1/36*     (2006.01)
*A61N 1/05*     (2006.01)
(Continued)

(52) U.S. Cl.
CPC ..... *A61N 1/36164* (2013.01); *A61N 1/36071* (2013.01); *A61N 1/36132* (2013.01);
(Continued)

(58) Field of Classification Search
CPC ................ A61N 1/0534; A61N 1/0551; A61N 1/36071; A61N 1/36132; A61N 1/36139;
(Continued)

(56) References Cited

U.S. PATENT DOCUMENTS 5,697,958 A  12/1997 Paul et al.
5,702,429 A  12/1997 King
(Continued)

FOREIGN PATENT DOCUMENTS

WO  2015/077362 A1  5/2015
WO  2015/143509 A1  10/2015
(Continued)

OTHER PUBLICATIONS

"Precision Spectra™ System Programming Manual," Boston Scientific Corp., 90834018-18 Rev A (2016).
(Continued)

*Primary Examiner* — George Manuel
(74) *Attorney, Agent, or Firm* — Lewis & Reese, PLLC

(57) ABSTRACT

Medical device systems and methods for providing spinal cord stimulation (SCS) are disclosed. The SCS systems and methods provide therapy below the perception threshold of the patient. The methods and systems are configured to measure neurological responses to stimulation and use the neurological responses as biomarkers to maintain and adjust therapy. An example of neurological responses includes an evoked compound action potential (ECAP).

20 Claims, 8 Drawing Sheets

(51) Int. Cl.
*A61N 1/372* (2006.01)
*A61N 1/375* (2006.01)

(52) U.S. Cl.
CPC ........ *A61N 1/36139* (2013.01); *A61N 1/0534* (2013.01); *A61N 1/0551* (2013.01); *A61N 1/36178* (2013.01); *A61N 1/36185* (2013.01); *A61N 1/3758* (2013.01); *A61N 1/37247* (2013.01)

(58) Field of Classification Search
CPC ............ A61N 1/36164; A61N 1/36178; A61N 1/36185; A61N 1/37247; A61N 1/3758
See application file for complete search history.

(56) References Cited

U.S. PATENT DOCUMENTS

| | | |
|---|---|---|
| 5,902,236 A | 5/1999 | Iversen |
| 5,902,249 A | 5/1999 | Lyster |
| 5,913,882 A | 6/1999 | King |
| 6,181,969 B1 | 1/2001 | Gord et al. |
| 6,516,227 B1 | 2/2003 | Meadows et al. |
| 7,024,247 B2 | 4/2006 | Gliner et al. |
| 7,424,322 B2 | 9/2008 | Lombardi et al. |
| 7,450,992 B1 | 11/2008 | Cameron |
| 8,255,057 B2 | 8/2012 | Fang et al. |
| 8,335,664 B2 | 12/2012 | Eberle |
| 8,352,030 B2 | 1/2013 | Denison |
| 8,606,362 B2 | 12/2013 | He et al. |
| 8,620,436 B2 | 12/2013 | Parramon et al. |
| 8,768,453 B2 | 7/2014 | Parramon et al. |
| 9,044,155 B2 | 6/2015 | Strahl |
| 9,061,140 B2 | 6/2015 | Shi et al. |
| 9,119,964 B2 | 9/2015 | Marnfeldt |
| 9,155,892 B2 | 10/2015 | Parker et al. |
| 9,248,274 B2 | 2/2016 | Troosters et al. |
| 9,248,279 B2 | 2/2016 | Chen et al. |
| 9,265,431 B2 | 2/2016 | Hincapie Ordonez et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,403,013 B2 | 8/2016 | Walker et al. |
| 9,409,020 B2 | 8/2016 | Parker |
| 9,526,897 B2 | 12/2016 | Chen et al. |
| 9,533,148 B2 | 1/2017 | Carcieri et al. |
| 9,597,507 B2 | 3/2017 | Johanek et al. |
| 9,623,250 B2 | 4/2017 | Lee et al. |
| 9,731,116 B2 | 8/2017 | Chen |
| 9,872,990 B2 | 1/2018 | Parker et al. |
| 9,974,455 B2 | 5/2018 | Parker et al. |
| 10,076,667 B2 | 9/2018 | Kaula et al. |
| 2002/0156513 A1 | 10/2002 | Borkan |
| 2005/0246004 A1 | 11/2005 | Cameron et al. |
| 2008/0077192 A1* | 3/2008 | Harry ................... A61N 1/0484 607/48 |
| 2008/0146894 A1 | 6/2008 | Bulkes et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0194772 A1 | 7/2014 | Single et al. |
| 2014/0236042 A1 | 8/2014 | Parker et al. |
| 2014/0277282 A1 | 9/2014 | Jaax |
| 2014/0296737 A1 | 10/2014 | Parker et al. |
| 2015/0032181 A1 | 1/2015 | Baynham et al. |
| 2015/0157861 A1 | 6/2015 | Aghassian et al. |
| 2015/0282725 A1 | 10/2015 | Single et al. |
| 2015/0313487 A1 | 11/2015 | Single et al. |
| 2015/0360038 A1 | 12/2015 | Zottola et al. |
| 2016/0082251 A1 | 3/2016 | Moffitt et al. |
| 2016/0082262 A1 | 3/2016 | Parramon et al. |
| 2016/0082268 A1 | 3/2016 | Hershey et al. |
| 2016/0166164 A1 | 6/2016 | Obradovic et al. |
| 2016/0287126 A1 | 10/2016 | Parker et al. |
| 2016/0287182 A1 | 10/2016 | Single et al. |
| 2017/0049345 A1 | 2/2017 | Single et al. |
| 2017/0071490 A1 | 3/2017 | Parker et al. |
| 2017/0135624 A1 | 5/2017 | Parker et al. |
| 2017/0216587 A1 | 8/2017 | Parker et al. |
| 2017/0296823 A1 | 10/2017 | Hershey et al. |
| 2017/0361101 A1 | 12/2017 | Single et al. |
| 2018/0071520 A1 | 3/2018 | Weerakoon et al. |
| 2018/0071527 A1 | 3/2018 | Feldman et al. |
| 2018/0110987 A1 | 4/2018 | Parker et al. |
| 2018/0117335 A1 | 5/2018 | Parker et al. |
| 2018/0132747 A1 | 5/2018 | Parker et al. |
| 2018/0132760 A1 | 5/2018 | Parker et al. |
| 2018/0133459 A1 | 5/2018 | Parker et al. |
| 2018/0140831 A1 | 5/2018 | Feldman et al. |
| 2018/0228391 A1 | 8/2018 | Parker et al. |
| 2018/0228547 A1 | 8/2018 | Parker et al. |
| 2018/0256052 A1 | 9/2018 | Parker et al. |
| 2019/0099602 A1 | 4/2019 | Esteller et al. |

FOREIGN PATENT DOCUMENTS

| | | |
|---|---|---|
| WO | 2017/100866 | 6/2017 |
| WO | 2017/173493 | 10/2017 |
| WO | 2017/210352 A1 | 12/2017 |
| WO | 2017/219096 | 12/2017 |

OTHER PUBLICATIONS

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302 pp. 60-73 (2013).

Part No. MSP430, manufactured by Texas Instruments, which is described in data sheets at http://www.ti.com/lsds/ti/microcontroller/16-bit_msp430/overview.p.? DCMP=MCU_other&HQS=msp430.

Crosby, Nathan D., John J. Janik, and Warren M. Grill, "Modulation of activity and conduction in single dorsal column axons by kilohertzfrequency spinal cord stimulation," Journal of neurophysiology 117.1 (2017): 136-147.

Shechter, Ronen, et al., "Conventional and kilohertz-frequency spinal cord stimulation produces intensityand frequency-dependent inhibition of mechanical hypersensitivity in a rat model of neuropathic pain," The Journal of the American Society of Anesthesiologists, 119.2 (2013): 422-432.

Song, Zhiyang, et al, "Efficacy of KilohertzFrequency and Conventional Spinal Cord Stimulation in Rat Models of Different Pain Conditions," Neuromodulation: Technology at the Neural Interface, 17.3 (2014): 226-235.

Invitation to Pay Additional Fees regarding corresponding PCT Application No. PCT/US2019/012058, dated Apr. 18, 2019.

U.S. Appl. No. 62/641,748, Zhu et al., filed Mar. 12, 2018.
U.S. Appl. No. 62/648,231, Esteller et al., filed Mar. 26, 2018.
U.S. Appl. No. 62/650,844, Marnfeldt et al., filed Mar. 30, 2018.
U.S. Appl. No. 62/679,259, Esteller et al., filed Jun. 1, 2018.
U.S. Appl. No. 62/768,617, Esteller et al., filed Nov. 16, 2018.
U.S. Appl. No. 62/825,982, Wagenbach et al., filed Mar. 29, 2019.
U.S. Appl. No. 16/210,794, Brill et al., filed Dec. 5, 2018.
U.S. Appl. No. 16/238,151, Esteller et al., filed Jan. 2, 2019.

H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).

M. Moffit et al., A Novel 3-Dimensional Algorithm for Model-Based Programming in Spinal Cord Stimuation (SCS): Illumina-3D™, presentation (2013).

J. Rubinstein et al., "Pseudospontaneous activity: stochastic independence of auditory nerve fibers with electrical stimulation," Hear Res, 127 (1-2), pp. 108-18 (1999) (abstract only).

J. Paz., "Physiological Midline Mapping Based on Spinal Cord Stimulation (SCS) Response Using the 32-Contact Paddle Lead," 19th NANS Annual Meeting (Dec. 13-15, 2015).

(56) References Cited

OTHER PUBLICATIONS

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

\* cited by examiner

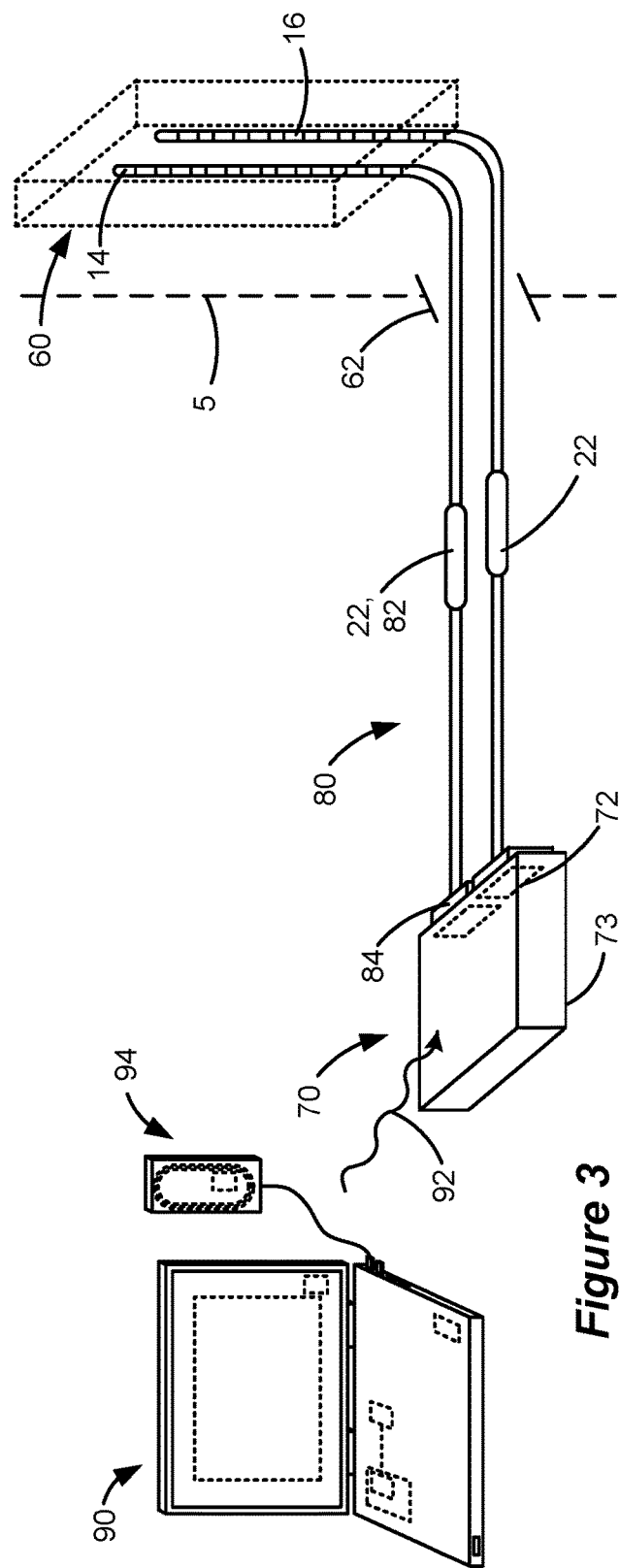
*Figure 3*
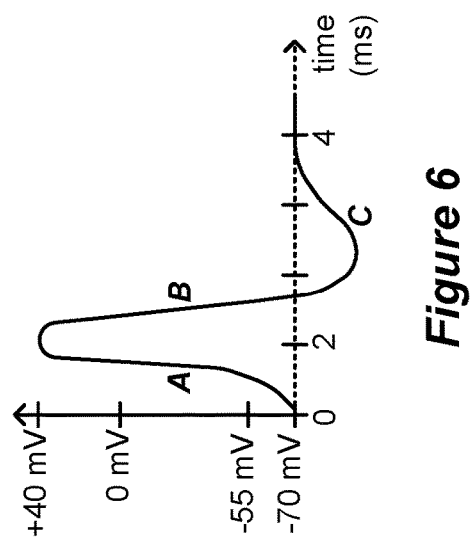
*Figure 5A*
*Figure 5B*
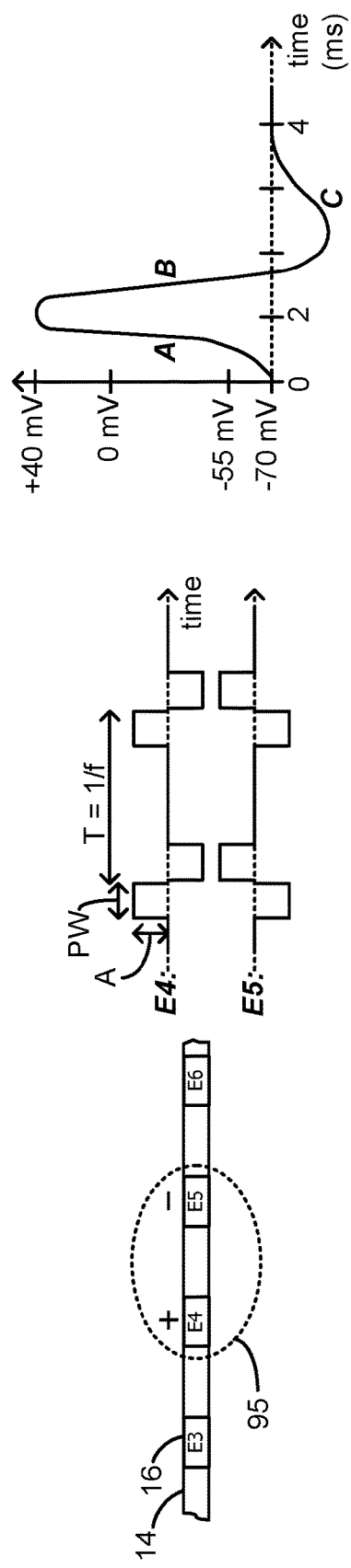
*Figure 6*

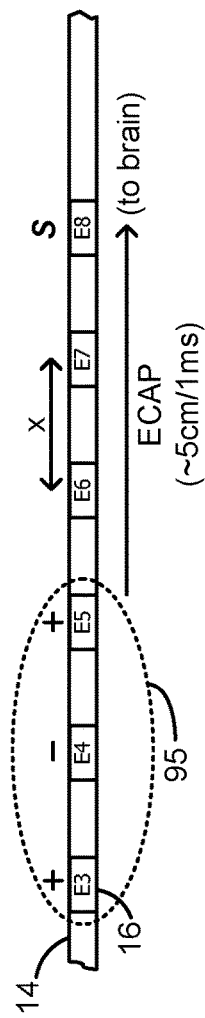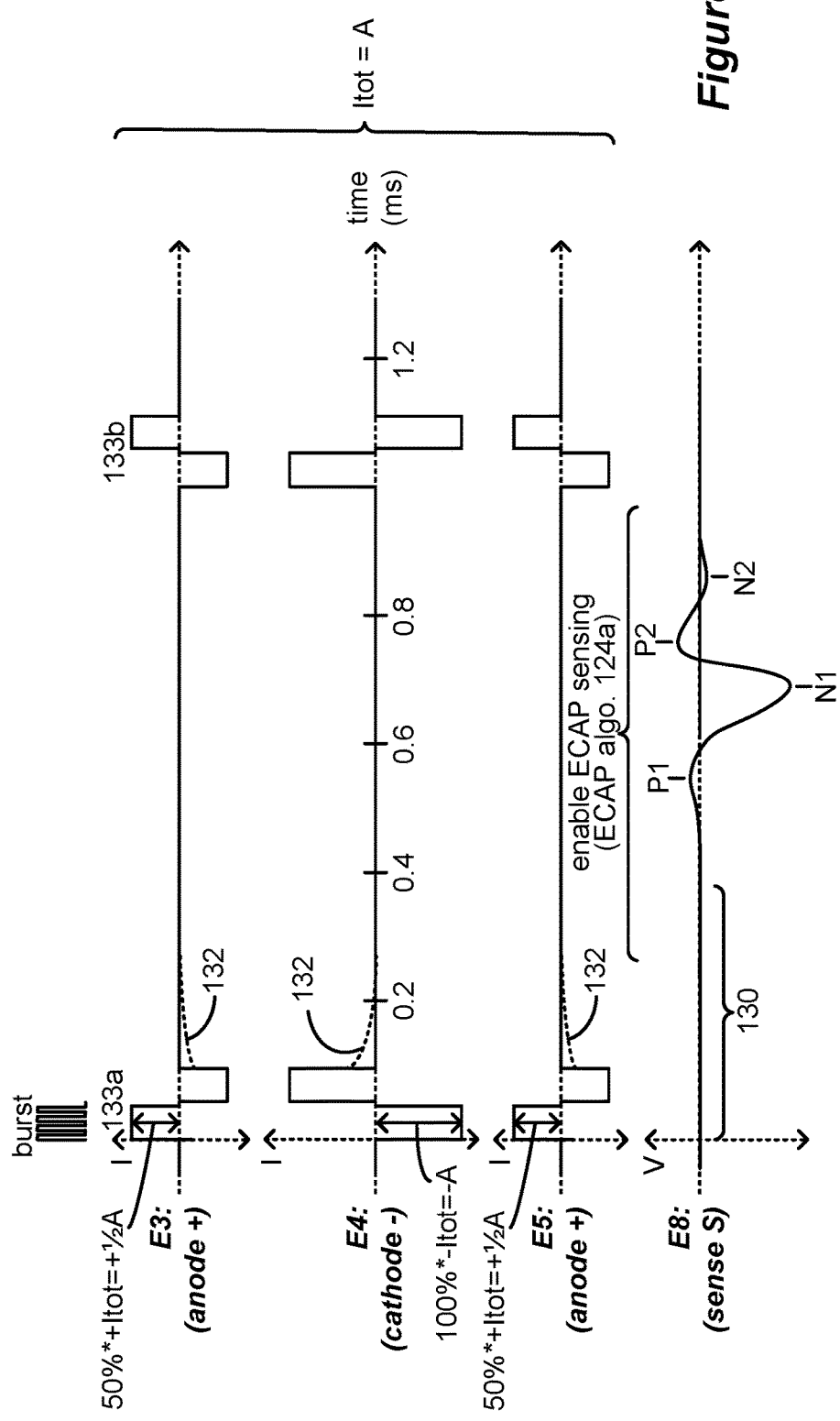
Figure 7A
Figure 7B

AUTOMATIC ADJUSTMENT OF SUB-PERCEPTION THERAPY IN AN IMPLANTABLE STIMULATOR USING DETECTED COMPOUND ACTION POTENTIALS

CROSS REFERENCE TO RELATED APPLICATIONS

This is a non-provisional of U.S. Provisional Patent Application Ser. No. 62/614,736, filed Jan. 8, 2018, which is incorporated herein by reference in its entirety, and to which priority is claimed.

FIELD OF THE INVENTION

The present invention relates generally to medical device systems, and more particularly to neurostimulator systems operable to measure central or peripheral nervous system potentials in the form of compound action potentials either evoked or not by a controlled stimulus or in the form of local field potentials both of which can be used to adjust stimulation therapy.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, sacral nerve stimulators to treat overactive bladder or bladder emptying problems, vagus nerve stimulators to treat epilepsy, trigeminal nerve stimulators to treat migraine and epilepsy, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which can be inserted into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14 (referred to as percutaneous leads), with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty-two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; a telemetry antenna—42a and/or 42b—for wirelessly communicating data with an external controller 50 (FIG. 2); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2), or a clinician programmer 90 (FIG. 3). Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS).

Implantation of IPG 10 in a patient is normally a multi-step process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

The stimulation program executed by the ETS 70 can be provided or adjusted via a wired or wireless link 92 (wireless shown) from a clinician programmer 90. As shown, the clinician programmer 90 comprises a computer-type device, and may communicate wirelessly with the ETS 70 via link 92, which link may comprise magnetic inductive or short-range RF telemetry schemes as already described. Should the clinician programmer 90 lack a communication antenna, a communication head or wand 94 may be wired to the computer which has a communication antenna. Thus, the ETS 70 and the clinician's programmer 90 and/or its communication head 94 may include antennas compliant with the telemetry scheme chosen. Clinician programmer 90 may be as described in U.S. Patent Application Publication 2015/0360038. External controller 50 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure. By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined during the trial stimulation phase, it/they can then be programmed into the IPG 10, and thereafter modified wirelessly, using either the external programmer 50 or the clinician programmer 90.

SUMMARY

Medical device systems and methods are described herein. In a first example, a medical device is disclosed, which may comprise: a plurality of electrodes each configured to be electrically coupled in contact with a patient's tissue; and control circuitry configured to: control stimulation circuitry to issue a stimulation waveform pursuant to a stimulation program, wherein the stimulation waveform is formed to provide pain relief and to be below a perception threshold of the patient, determine a neural response to the stimulation waveform at at least one electrode of the plurality of electrodes and to determine at least one feature of the neural response, and based on the at least one feature, adjust the stimulation program so that the stimulation waveform stays below the perception threshold.

The neural response may comprise an Evoked Compound Action Potential (ECAP) or other longer latency neural responses. The at least one feature may be indicative of the shape and/or size of the ECAP. The at least one feature may comprise an ECAP peak height or width. The at least one feature may comprise an area of the ECAP or of any ECAP peak. The at least one feature may comprise a length of any portion of the ECAP. The at least one feature may comprise a time defining a duration of any portion of the ECAP, or a time delay from stimulation to issuance of the ECAP. According to some embodiments, the control circuitry determines the at least one feature of the neural response by comparing the at least one feature to at least one threshold or range. According to some embodiments, the control circuitry is configured to adjust the at least one threshold or range based on user input. According to some embodiments, the user input is telemetered from an external controller. According to some embodiments, the control circuitry further comprises at least one amplifier configured to amplify the neural response at the at least one electrode. According to some embodiments, the control circuitry further comprises at least one Analog-to-Digital converter configured to receive the output of the at least one amplifier and to digitize the amplified neural response. According to some embodiments, the control circuitry determines the threshold or range for different patient postures or body activities that allow the establishment of the threshold range.

A second example is a non-transitory computer-readable medium having instructions stored thereon to cause circuitry in a computing device to: cause a medical device to issue a first stimulation waveform pursuant to a first stimulation program using one or more of a plurality of electrodes each configured to be electrically coupled in contact with a patient's tissue, receive data from the medical device indicative of a first neural response to the first stimulation waveform at at least one electrode of the plurality of electrodes, cause the medical device to issue a second waveform pursuant to a second stimulation program using one or more of the plurality of electrodes, receive data from the medical device indicative of a second neural response to the second stimulation waveform at at least one electrode of the plurality of electrodes, determine at least one feature of the first and second neural responses that changes based on differences between the first and second stimulation programs, and determine at least one threshold or range of the at least one feature that correlates to a stimulation that provides pain relief and is below a perception threshold of the patient.

The neural response may comprise an Evoked Compound Action Potential (ECAP) or other longer latency neural responses. The at least one feature may be indicative of the shape and/or size of the ECAP. The at least one feature may comprise an ECAP peak height or width. The at least one feature may comprise an area of the ECAP or of any ECAP peak. The at least one feature may comprise a length of any portion of the ECAP. The at least one feature may comprise a time defining a duration of any portion of the ECAP, or a time delay from stimulation to issuance of the ECAP. The at least one threshold or range may comprise the perception threshold of the patient. The at least one threshold or range may comprise the minimum stimulation at which an ECAP is detectable. The non-transitory computer-readable medium may further comprise instructions stored thereon to cause the circuitry in a computing device to display information related to the data indicative of a second neural response. The non-transitory computer-readable medium may further comprise instructions stored thereon to cause the circuitry in a computing device to transmit the threshold or range to the medical device.

BRIEF DESCRIPTION OF THE DRAWINGS

FIG. 3 shows a clinician programming system for communicating with an IPG or an External Trial Stimulator (ETS).

FIGS. 5A and 5B illustrate a stimulation waveform.

FIG. 6 shows a graph of an action potential of a neuron.

FIGS. 7A and 7B illustrate an Evoked Compound Action Potential (ECAP) in response to neural stimulation.

DETAILED DESCRIPTION

Various embodiments described herein involve neural modulation. Examples of neural modulation include spinal cord stimulation (SCS), deep brain stimulation (DBS), peripheral nerve stimulation (PNS), vagus nerve stimulation (VNS), and sacral nerve stimulation for over active bladder (OAB).

Figure 4A:
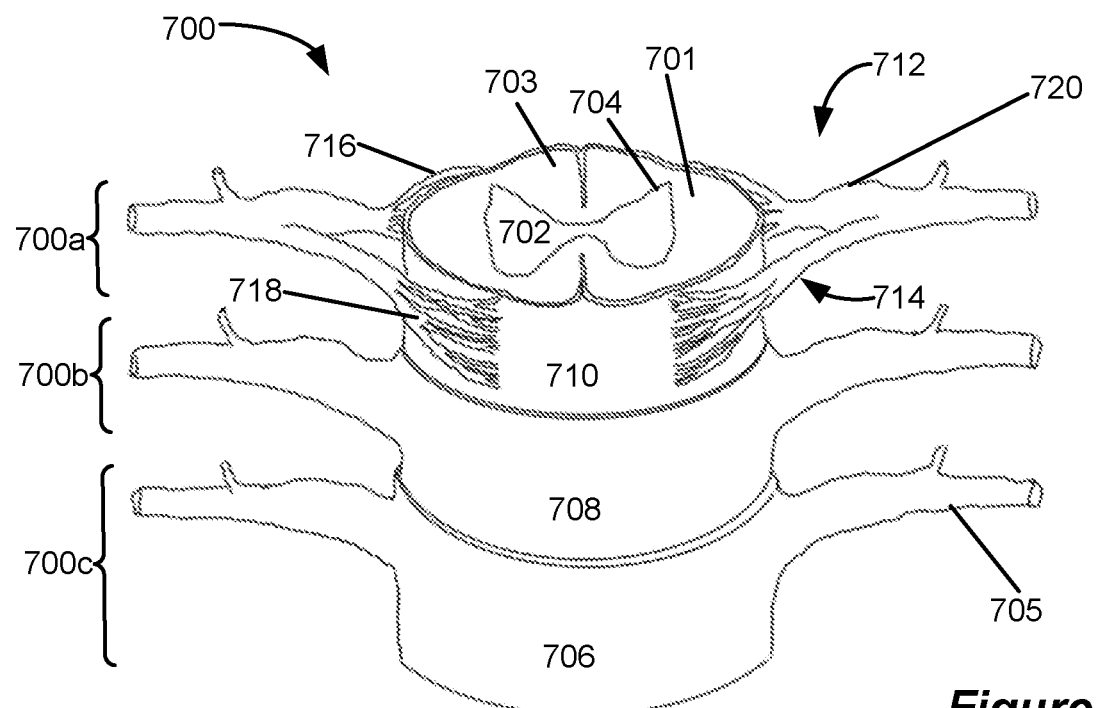
FIGS. 4A and 4B illustrate a spinal cord and related neural anatomy.
Figure 4B:
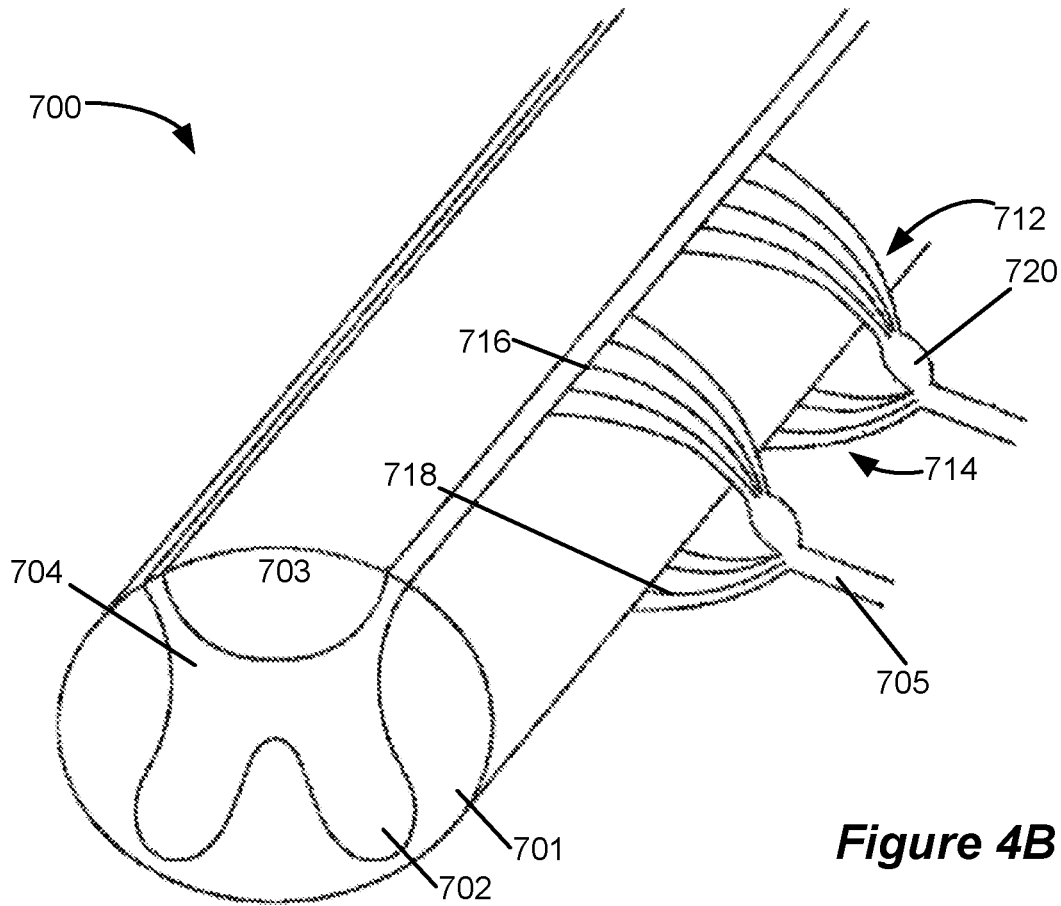

A brief description of the physiology of the spinal cord is provided herein to assist the reader with regard to embodiments involving SCS. FIGS. 4A and 4B illustrate, by way of example, a portion of a spinal cord 700 including white matter 701 and gray matter 702 of the spinal cord. The gray matter 702 includes cell bodies, synapse, dendrites, and axon terminals. Synapses are located in the gray matter. White matter 701 includes myelinated axons that connect gray matter areas. A typical transverse section of the spinal cord includes a central "butterfly" shaped central area of gray matter 702 substantially surrounded by an ellipse-shaped outer area of white matter 701. The white matter of the dorsal column (DC) 703 includes mostly large myelinated axons that form afferent fibers that run in an axial direction. The dorsal portions of the "butterfly" shaped central area of gray matter are referred to as dorsal horns (DH) 704. In contrast to the DC fibers that run in an axial direction, DH fibers can be oriented in many directions, including laterally with respect to the longitudinal axis of the spinal cord.

Referring to FIG. 4A, the spinal cord is enclosed within three layers of tissue, collectively called the meninges. The outer layer of the meninges, called the dura mater 706, is shown in spinal cord segment 700c. The dura mater has been removed in spinal cord segment 700b to reveal the middle meninges, called the arachnoid 708. The innermost meninges, the pia mater 710, is shown in spinal cord segment 700a.

Examples of spinal nerves 705 are also illustrated. Upon removal of the meningeal layers, it is seen that each spinal nerve 705 splits into a dorsal root (DR) 712 and a ventral root 714, each of which comprise subdivisions referred to as rootlets. In FIG. 4A, the dorsal rootlets are labeled 716 and the ventral rootlets are labeled 718. The dorsal root also includes a structure called the dorsal root ganglion (DRG) 720, which comprises cell bodies of the afferent neurons. The dorsal root 712 contains afferent neurons, meaning that they carry sensory signals into the spinal cord, and the ventral root 714 functions as an efferent motor root. The dorsal and ventral roots join to form mixed spinal nerves 705.

An example of stimulation pulses as prescribed by an example stimulation program and as executable by the IPG or ETS 70 is illustrated in FIGS. 5A and 5B. As shown in FIG. 5A, electrode E4 is selected as the anode and electrode E5 is selected as the cathode. FIG. 5B illustrates the waveforms of the stimulation pulses delivered by E4 and E5. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses—having only a first pulse phase but not followed by an active-charge recovery second pulse phase—can also be used.

The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

When a neural element is recruited by electrical stimulation, it will issue an action potential—that is, the neural element will "fire." An action potential for a typical neural element is shown in FIG. 6. Should electrical recruitment from electrical stimulation cause the neural membrane's resting state (e.g., −70 mV as measured from inside the cell) to exceed a threshold (e.g., −55 mV), the neural element will depolarize ("A"), repolarize ("B"), and hyperpolarize ("C") before coming to rest again. If electrical stimulation continues, the neural element will fire again at some later time, though the neural element cannot fire again until after the membrane potential returns to the resting state after the hyperpolarization event. Note that the action potential does not change in magnitude for a given neural element. Instead, changing the strength of stimulation may affect the number of action potentials that are issued, with higher magnitudes eliciting more action potentials and may also affect what types of neural elements and fibers are recruited. Each neural element is unique in its type and size, and thus can transmit the action potential at its own inherent speed. Fibers with bigger diameter transmit the action potential faster than smaller diameter fibers. The temporal and spatial summation of action potentials synchronously firing in response to an evoked stimulus produces a CAP (Compound Action Potential) response.

Current implantable neuromodulation systems typically include electrodes implanted adjacent, i.e., resting near, or upon the dura mater 706, of the dorsal column of the spinal cord of the patient and along a longitudinal axis of the spinal cord of the patient. A therapeutic goal for conventional SCS programming has been maximum stimulation (i.e., recruitment) of the DC fibers that run in the white matter along the longitudinal axis of the spinal cord and minimal stimulation of other fibers that run perpendicular to the longitudinal axis of the spinal cord such as the dorsal root fibers or ventral root fibers. The white matter of the DC 703 includes mostly large myelinated axons that form afferent fibers, i.e., fibers carrying sensory signals to the brain.

While the full mechanisms of pain relief are not well understood, it is believed that the perception of pain signals is inhibited via the gate control theory of pain, which suggests that enhanced activity of innocuous touch or pressure primary afferents fibers via electrical stimulation creates interneuronal activity within the DH 704 of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at amplitudes that provide pain relief.

Activation of large sensory DC nerve fibers in conventional SCS creates action potentials (i.e., nerve impulses) that propagate orthodromically (toward the brain) and antidromically (away from the brain) from the point of stimulation. The antidromic propagation of action potentials to fiber collaterals and terminals ending in the DH evokes pain control mechanisms within the DH, as described above. The orthodromic propagation of action potentials is responsible for the paresthesia sensation that often accompanies conventional SCS therapy. Although such paresthesia is usually tolerated relative to the sensation of pain, patients sometimes report these sensations to be uncomfortable, and therefore, they can be considered an adverse side-effect of neuromodulation therapy in some cases.

Some SCS embodiments deliver sub-perception therapy that is therapeutically effective to treat pain, for example, but wherein the patient does not sense the delivery of the modulation field (e.g. paresthesia). Sub-perception therapy can be delivered at any frequency below 1 Hz or above 1 Hz and may include higher frequency modulation (e.g. about 1000 Hz or above) of the spinal mechanisms producing pain relief, likely by interfering with the transmission of pain signals. Some embodiments herein selectively modulate DH neural targets or DR neural targets over DC targets to provide sub-perception therapy. Embodiments of sub-perception therapy are described in U.S. Patent Application Publication Nos. 2016/0082262, 2016/0082251, and 2016/0082268, the contents of which are incorporated herein by reference.

The orthodromic and/or antidromic propagation of action potentials described above can be sensed using electrodes. FIGS. 7A and 7B illustrate how evoked compound action potentials (ECAPs) evoked during stimulation are sensed using a sense electrode on a lead 14. It should be noted that aspects of ECAP sensing such as choosing which electrodes to use as sense electrodes, when and how to sense, etc., may be implemented based on one or more algorithms (referred to herein as "ECAP algorithms") comprised within the IPG 100 (or ETS 170, see FIGS. 1 and 2) and/or within the clinician's programmer. The ECAP algorithm is described in more detail below, though aspects of the ECAP algorithm are discussed here with reference to FIGS. 7A and 7B.

Consider FIG. 7A, in which electrodes E3, E4 and E5 on lead 14 are used to produce pulses in a bipolar mode of stimulation, with E3 and E5 comprising anodes (+; or source of current) and E4 a cathode (−; or sink of current). Such stimulation produces an electromagnetic (EM) field in a volume 95 of the patient's tissue around the selected electrodes. Some of the neural elements within the EM field volume 95 will be recruited and fire, particularly those proximate to the cathodic electrode E4. Hopefully the sum of the neural elements firing within volume 95 will mask signals indicative of pain in an SCS application, thus providing the desired therapy.

The stimulation program is defined by various stimulation parameters to form stimulation pulses, such as which electrodes are active for stimulation, the polarity of those electrodes, the amplitude at selected electrodes, pulse width at each pulse phase, pulse frequency, cycling, and stimulation waveform shape (square pulses in the example shown), although these parameters are not all labeled in FIG. 7B. In the example stimulation program shown, and considering only the first phase of the biphasic pulses, electrode E4 is selected to operate as a cathode (−), and electrodes E3 and E5 are selected to operate as anodes (+). Such stimulation is usually referred to as tripolar stimulation. Tripolar and bipolar stimulation are some of the preferred modes of providing stimulation, particularly in an SCS application, because neural fibers in the dorsal column are activated proximate to the cathode while using the anodes as flanking regions. Anodic activation exhibits a higher threshold compared to cathodal stimulation. An embodiment to use anodic activation can be used by placing the cathode electrode in the device can.

In the example shown, the pulses are defined with respect to a total anodic and cathodic current (collectively, Itot) that the electrodes will provide at any given time. This is desirable so that the patient's tissue will not receive a net amount of charge. The sole cathode electrode E4 provides all the total cathodic current (−Itot), and so provides 100*−Itot, or −A. The two anode electrodes E3 and E5 must together issue the total anodic current (+Itot), and in this example each provides 50%*+Itot, or +A/2. The anode electrodes can issue any anodic currents that together will equal +Itot (e.g., 70%*+Itot and 30%*+Itot). It is assumed that this stimulation program has been chosen as one that generally provides good therapeutic results for a particular patient.

Neural elements that are recruited and that fire within volume 95 create a cumulative response called an Evoked Compound Action Potential, or ECAP. Once stimulation begins (at time=0), an ECAP will be produced comprising the sum of the action potentials of neural elements recruited and hence firing in volume 95. As shown in FIG. 7B, the ECAP will move through the patient's tissue via neural conduction with speeds of about 3.3-7.5 cm/ms in the typical case of Aβ fibers, or 0.3-3.5 cm/ms in the case of Aδ fibers. In the example shown, the ECAP moves to the right, which is in an orthodromic direction toward the brain (rostrally). However, the ECAP will also move in the antidromic direction as well toward the bottom of the spinal cord of the patient (caudally).

The amplitude of an ECAP will depend on how many neural elements are firing. Generally speaking, a primary ECAP response, e.g., the height of peaks P1, N1, and P2 (see FIG. 8), can vary, usually between tens of microVolts to tens of milliVolts. Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is within a range that the control circuitry 102 in the IPG 100 can handle, such as between 3 Volts and ground.

It should be noted here that compound action potentials may be evoked in various neural elements, including the neural fibers of the dorsal column, the dorsal root fibers, the dorsal root ganglia, etc. As used herein, the ECAP refers to action potentials evoked in any of the neural elements.

Referring again to FIGS. 7A and 7B, the ECAP algorithm has chosen a single sense electrode (S) has been chosen to sense the ECAP as it moves past, which in this example is electrode E8. Selection of an appropriate sense electrode can be based on a number of factors. For example, it is preferable that a sense electrode S be sensibly chosen with respect to the active electrodes, such that the EM field produced around the active electrodes will dissipate (or more preferably, cease) at the sense electrode by the time the ECAP arrives. This simplifies ECAP detection at the sense electrode, because voltages present in the EM field will not interfere with and potentially mask the ECAP at the sense electrode. (Note that the stimulation artifact resulting from the EM field is not shown at the sense electrode E8 for simplicity). However, it should be noted that the stimulation artifact decreases in magnitude as the distance from the stimulation electrode increases. Therefore, the optimal sensing electrode(s) may be chosen to maximize the ECAP response and minimize the artifact voltage.

Figure 1A:
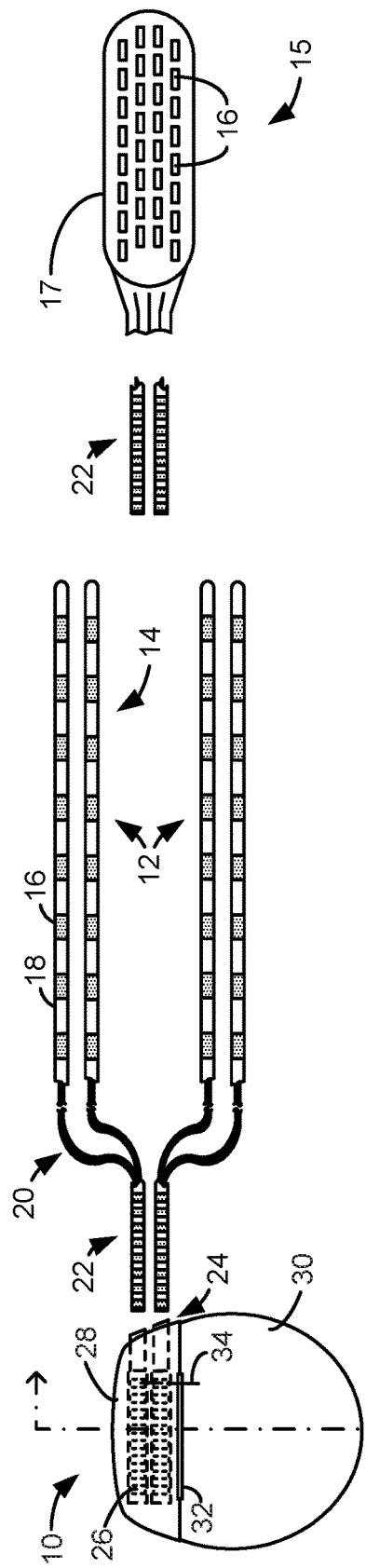
FIGS. 1A and 1B respectively show an Implantable Pulse Generator (IPG) in plan and cross-sectional views.
Figure 1B:
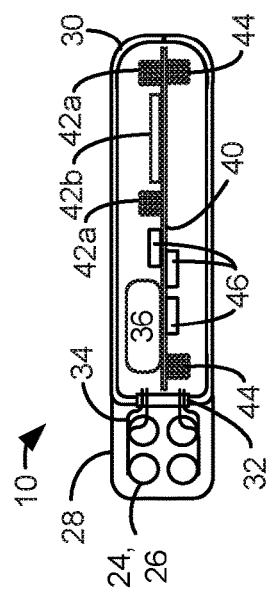

To choose a sense electrode, the ECAP the algorithm (described below) preferably knows the pulse width of the pulses being issued, the extent of the size of the EM field (which can be estimated), the speed at which the ECAP is expected to travel, and the distance (x) between electrodes 16 in the electrode array 12, e.g., along a particular straight lead 14 or a paddle lead 15 (FIG. 1A).

According to some embodiments, it is not strictly necessary that sensing occur at an electrode that would not experience interference from the EM field produced by the active electrodes, because masking techniques can be used to subtract voltages present in the EM field. Such masking techniques are described for example in M. Hughes, "Fundamentals of Clinical ECAP Measures in Cochlear Implants: Part 1: Use of the ECAP in Speech Processor Programming (2nd Ed.)," Audiology Online (Nov. 8, 2010) (http:// www.audiologyonline.com/articles/fundamentalsclinicale-capmeasuresin846); and I. Akhoun et al., "Electrically evoked compound action potential artifact rejection by independent component analysis: Technique validation," Hearing Research 302 pp. 60-73 (2013), which are both incorporated herein by reference. In fact, an active electrode can be used for ECAP sensing, which would involve quickly disconnecting the stimulation circuitry from the electrodes (e.g., at the switch matrix 106, FIG. 8) and quickly connecting the electrodes to the sensing circuitry (e.g., using MUX 108, FIG. 8).

Referring again to FIGS. 7A and 7B, assume that the pulse width (of both phases of the biphasic pulses) is 0.1 ms as shown, and that sense electrode E8 is generally 2.0 cm away from the active electrodes (and hence their EM field). When the ECAP starts to form at time=0, it will arrive at electrode E8 after some delay 130 in accordance with the speed at which the ECAP moves (e.g., 5 cm/1 ms). In this example, the ECAP will start to pass sense electrode E8 at 0.4 ms. Thus, the ECAP algorithm can thus enable sensing of the ECAP starting at or before time=0.4 ms after the start of the stimulation pulse. Sensing can last for as long as necessary to detect at least some aspects of the shape and size of the resulting ECAP. For example, sensing can last for a long enough time to allow the polarization and refraction peaks in the ECAP to be detected, which may comprise up to 3 ms for example. If the total duration of the ECAP is longer than the quiet period between two subsequent pulses, e.g., between pulses 133a and 133b, the ECAP algorithm may not enable subsequent stimulation pulses 133b until the ECAP measurement has finished.

Figure 8:
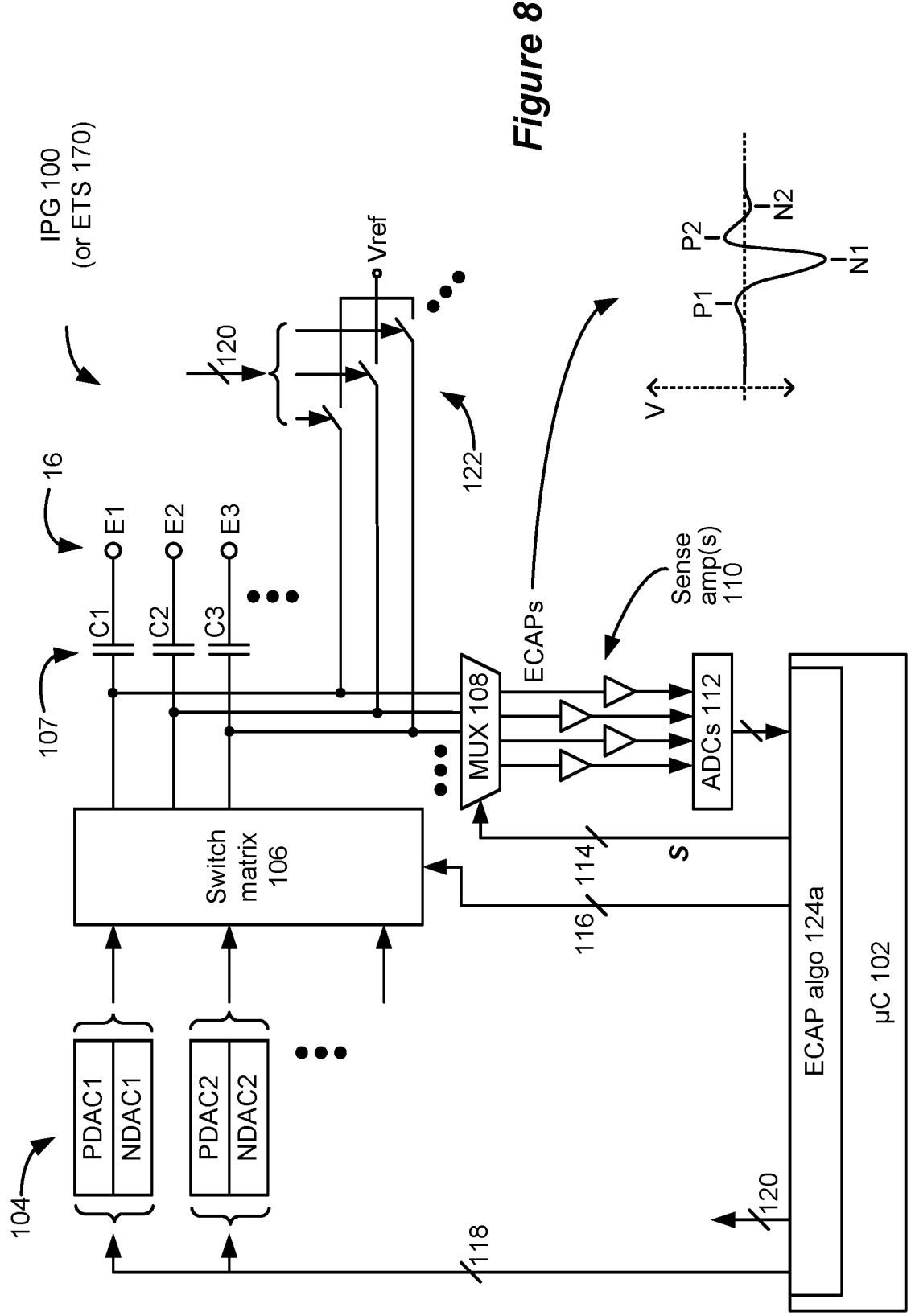
FIG. 8 shows an improved IPG (or ETS) including control circuitry programmed with an Evoked Compound Action Potential (ECAP) algorithm, and further including sensing circuitry for sensing an ECAP at a sense electrode.

FIG. 8 shows circuitry for an improved IPG 100 operable with the disclosed technique for sensing ECAP and using the sensed ECAP as a biomarker for directing therapy, as described further below. Although described in the context of an IPG 100, it should be realized that the disclosed technique could also be operable in an improved external stimulator, such as an External Trial Stimulation 170 that generally mimics the operation of an IPG as explained earlier.

The IPG 100 (or ETS 170) includes control circuitry 102 into which an ECAP algorithm 124a can be programmed. Control circuitry 102 may comprise a microcontroller for example such as Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and U.S. Pat. Nos. 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The illustrated circuitry for producing stimulation pulses and delivering them to the electrodes is merely one example. Other approaches may be found for example in U.S. Pat. Nos. 8,606,362 and 8,620,436, and U.S. Patent Application Publication 2018/0071520. Note that a switch matrix 106 isn't required, and instead a PDAC and NDAC can be dedicated to (e.g., wired to) each electrode.

Notice that the current paths to the electrodes 16 include the DC-blocking capacitors 107, which as known, provide additional safety by preventing the inadvertent supply of DC current to an electrode and to a patient's tissue. As discussed earlier, capacitances such as these can become charged as stimulation currents are provided, providing an impetus for the use of biphasic pulses.

One or more of the electrodes 16 can be used to sense the ECAP as described earlier, and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP, described further below, is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs.

Note that the ECAP algorithm 124a can enable measurement of an ECAP after a single pulse, or after a train of (higher-frequency) pulses. If necessary, more than one ECAP can be measured after subsequent pulses or trains of pulses and averaged to improve the fidelity of the signal. Further, pre-processing can occur prior to measuring the ECAP, as explained further below. Although FIGS. 7A and 7B show active electrodes and a sense electrode on a single lead 14, this is not required, and any active electrodes and sense electrodes can be chosen in an electrode array 12, including two-dimensional arrays provided by more than one lead 14, or on a single paddle lead 15 (FIG. 1A). The conductive case 30 (FIG. 1B) can also be used as a sensing electrode.

The ECAP algorithm 124a could choose more than one electrode to act as a sense electrode. For example, ECAP algorithm 124a may sense the traveling ECAP at electrodes E6, E7, E8, E9, etc. This would require timing control, because E6 would sense before E7, etc., and might further require circuitry changes to accommodate sensing the ECAP at different electrodes at overlapping points in time. For example, each electrode might in this example require its own timing control (mux 108), and its own sense amp 110 and ADC 112, although this isn't illustrated in FIG. 8. Use of more than one sense electrode can be useful, as this allows the speed of the neural conduction to be calculated (if the electrode distance x is known). ECAP speed may indicate the types of neural fibers that are being recruited, which may in turn be useful to deciding how stimulation therapy in the IPG 100 (or ETS 170) might be adjusted, as explained further below.

A practical aspect that could affect sensing ECAPs in IPG 100 (or ETS 170) relates to passive charge recovery. As discussed earlier, the use of biphasic pulses are preferred in an IPG to actively recover charge during the second pulse phase that may have built up across capacitive elements (such as the DC blocking capacitors 107) during the first pulse phase. Because active charge recovery may not be perfect, IPG 100 may additionally include passive charge recovery as implemented by switches 122 shown in FIG. 8. Note that passive charge recovery can also be used following monophasic pulses. Passive charge recovery switches 122 are controlled by bus 120 issued from the control circuitry 102, and act to connect the inside plate of the DC blocking capacitors 107 to a common potential (Vref). When this occurs, the DC blocking capacitors 107 are connected in parallel between the common potential and the patient's tissue, which helps to equilibrate the charge across the capacitors and hence passively recover any remaining charge. Passive charge recovery using switches 122 typically occurs after the last phase of each stimulation pulse, as shown by the small, exponentially-decreasing waveforms 132 in FIG. 9B. Passive charge recovery might otherwise overlap in time with periods in which ECAP sensing is enabled. This could cause a problem for ECAP sensing, because it would place the common potential on the inputs to the multiplexer 108 that carry the ECAP signals. As a result, control circuitry 102 may wait to enable ECAP sensing until passive recovery (closing of switches 122) has finished. Alternatively, control circuitry 102 will preferably not close the passive recovery switch 122 associated with the sense electrode when an ECAP is to be sensed, although all other switches 122 may be closed. Once the ECAP has been sensed, control circuitry 102 may return to closing the sense electrode's switch 122 if desired.

Notice that connection of the electrodes 16 to the sense amp(s) 110 preferably occurs through the DC-blocking capacitors 107, such that capacitors are between the electrodes and the sense amp(s) 110. This is preferred so as to not undermine the safety provided by the DC-blocking capacitors 107.

Figure 9:
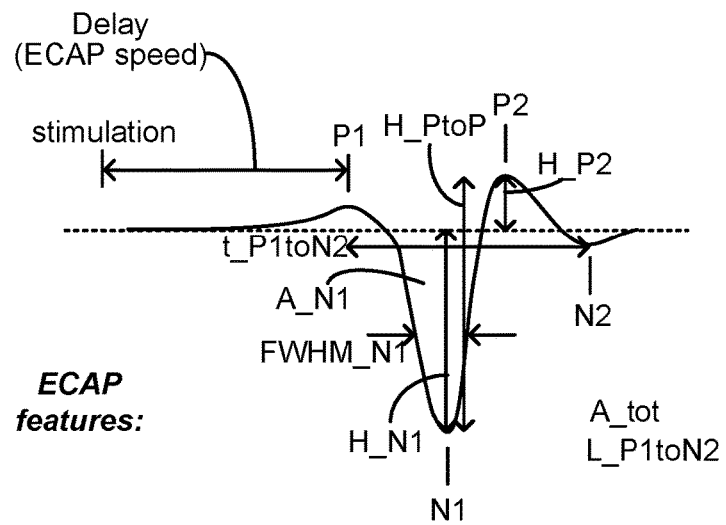
FIG. 9 shows features of an ECAP.

Once the digitized ECAP is received at the control circuitry 102, it is processed by the ECAP algorithm 124a to determine one or more ECAP features that describe the basic shape and size of the ECAP(s), as explained further below with reference to FIG. 9. The response to stimulation can include potentials observed at different delays corresponding to different type of neural elements recruited. The delay from the stimulus depends on the type of neural elements activated by the stimulus. Larger diameter fibers transmit the action potential at faster speeds than smaller diameter fibers. Therefore, the more distance between the sensing electrode and the stimulation electrode the bigger the expected delay. Neural elements include axon fibers, neuron cell bodies, neuron dendrites, axon terminals, locations where fiber collaterals branch, interneurons, glial cells, or any nervous system functional part. In the specific case of the spinal cord, the sense electrodes can be placed over the dorsal column, more laterally in the epidural space towards and over the edge of dorsal horn and/or Lissauer's tract, over the dorsal root entry zone (DREZ), the rootlets, the dorsal root ganglia (DRG), the cauda equina region, the spinal nerves close to the spinal cord, the Spino-thalamic tract, and any other of the tracts surrounding the gray matter of the spinal cord. An ECAP can contain a number of peaks or waves indicative of the different phases of the averaged or compound action potential sensed and depending on the delay with respect to the stimulus, the peak potentials can be indicative of different type of fibers activated. Axon fibers with different functions (C fibers, Aβ fibers, Aδ fibers, and others) have different diameters that correlate with different propagation velocities for the compound potentials. Conduction velocities for different axonal fiber types are known, and the conduction velocities of the ECAPs sensed in the spinal cord can be calculated to determine the originating fiber. As shown if FIG. 8, peaks in the ECAP are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 8 (and FIG. 9), because an ECAP's shape is a function of the number and types of neural fibers that are recruited in a given volume 95.

Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is within a range that the control circuitry 102 in the IPG 100 can handle, such as between 3 Volts and ground.

Figure 2:
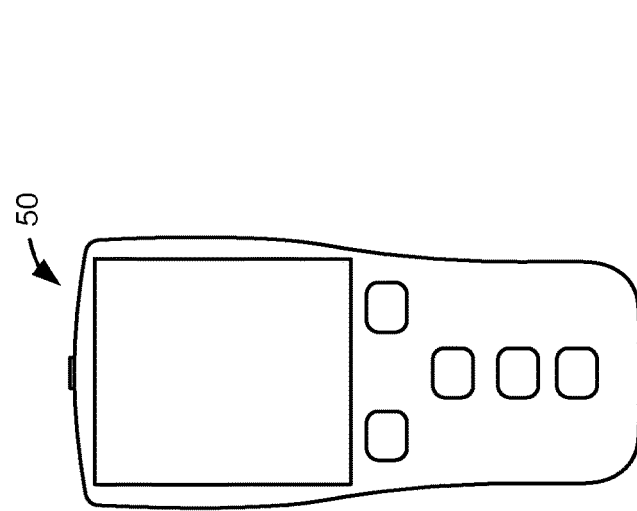
FIG. 2 shows a hand-held external controller for communicating with an IPG.

As discussed earlier, it is important to determine a stimulation program that will best alleviate a patient's symptoms. Part of this "fitting" process includes determining which electrodes should be activated by the IPG 100 (or the ETS 170); the polarity of these active electrodes; the amplitude of stimulation; (if stimulation is issued in pulses) the pulse width, frequency, the duty cycle (DC), and shape of the waveform (e.g., pulses); etc. Initial fitting of a patient to determine a stimulation program that is effective usually occurs using a clinician programmer 90 (FIG. 3), but fitting or stimulation program adjustment can also occur using a patient external controller 50 (FIG. 2). Fitting can occur both during an external trial phase as described earlier and after a permanent IPG 100 has been implanted.

Conventional programming for SCS therapy uses paresthesia to select an appropriate parameter set. The modulation for conventional SCS can be adjusted to map the paresthesia over the region of pain. However, sub-perception modulation can pose some challenges for selecting and refining the parameters for use to deliver the therapeutic modulation. For example, conventional SCS may simply try to provide a small targeted stimulation to modulate the DC and cause paresthesia. The modulation for conventional SCS can be adjusted to map the paresthesia over the region of pain. In other words, under the optimum parameters the patient may feel the pain in the affected area replaced by a tolerable tingling sensation. However, a patient does not perceive the delivery of the modulation energy for sub-perception modulation. Thus, simply mapping paresthesia to an area of pain is not an available option. Moreover, the clinical literature suggests that pain relief afforded by sub-perception therapy can occur via slow acting mechanisms. Wash-in and wash-out times may take hours to a couple days to evaluate and, in general, may take longer compared to traditional therapies that exceed the patient's perception threshold. Different patients respond to different therapy modalities; thus, assessment of various therapy options can be time consuming and resource intensive.

The inventors have discovered methods and systems for using evoked spinal cord potentials and evoked compound action potentials (ECAPs) to direct and adjust sub-perception therapy. More specifically, the methods and systems using ECAPs as biomarkers to elucidate neural recruitment and different neural fiber types, thereby providing a handle with which to direct therapy and how to effectively adjust therapy at sub-perception dosages when the patient is not aware the therapy is being delivered.

The inventor has discovered that when stimulating with small amplitudes using SCS percutaneous or paddle leads, there are ECAP responses not visible by naked eye, on the order of 10% or 14% of the noise floor of the spinal cord sensed signals (where the noise floor is determined when no stimulus is present), these ECAP responses are elicited at amplitudes lower than 50% motor threshold and can be extracted by signal processing techniques. These ECAP responses have even been observed at 10% of motor threshold. Note that the scientific community presently considers the perception threshold in animal experiments to generally be 50% of motor threshold. See, for example, Crosby, Nathan D., John J. Janik, and Warren M. Grill, "Modulation of activity and conduction in single dorsal column axons by kilohertz-frequency spinal cord stimulation," Journal of neurophysiology 117.1 (2017): 136-147; Shechter, Ronen, et al., "Conventional and kilohertz-frequency spinal cord stimulation produces intensity- and frequency-dependent inhibition of mechanical hypersensitivity in a rat model of neuropathic pain," The Journal of the American Society of Anesthesiologists, 119.2 (2013): 422-432; and Song, Zhiyang, et al, "Efficacy of Kilohertz Frequency and Conventional Spinal Cord Stimulation in Rat Models of Different Pain Conditions," Neuromodulation: Technology at the Neural Interface, 17.3 (2014): 226-235. The inventor developed a system and method that uses metrics derived from ECAP features evoked under various stimulation conditions to direct sub-perception therapy. Various features for an ECAP that can generate such metrics are shown in FIG. 9. These include (but are not limited to):

- a height of any peak (e.g., H_N1) present in the ECAP;
- a peak-to-peak height between any two peaks (such as H_PtoP from N1 to P2);
- a ratio of peak heights (e.g., H_N1/H_P2);
- a peak width of any peak (e.g., the full width half maximum of a N1, FWHM_N1);
- an area under any peak (e.g., A_N1);
- a total area (A_tot) comprising the area under positive peaks with the area under negative peaks subtracted or added;
- a length of any portion of the curve of the ECAP (e.g., the length of the curve from P1 to N2, L_P1toN2) where the length can be computed in several ways, such as (1) the absolute value of the difference of consecutive values in the ECAP signal; (2) the Euclidean distance formula applied to the non-distance y-axis (ECAP magnitude-axis) and x-axis (time-axis); (3) a pseudo distance formula given by absolute value of consecutive samples in the ECAP magnitude signal plus the absolute value of the difference of x-axis (time-axis) samples for the ECAP length defined; (4) any other distance definition that can be applied to assess the length of the ECAP of any portion of the curve of the ECAP magnitude.
- any time defining the duration of at least a portion of the ECAP (e.g., the time from P1 to N2, t_P1toN2);
- a time delay from stimulation to issuance of the ECAP, which is indicative of the neural conduction speed of the ECAP, and which can be useful in discerning the types of neural fibers recruited;
- any mathematical combination or function of these variables (e.g., H_N1/FWHM_N1 would generally specify a quality factor of peak N1).

Figure 10:
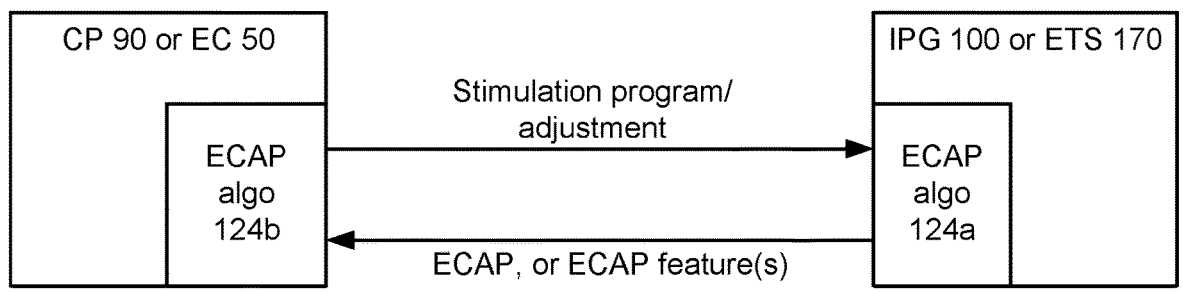
FIG. 10 shows aspects of an ECAP algorithm.

The systems and methods described herein identify one or more metrics based on one or more of the above features and use those metrics as biomarkers for optimizing and maintaining therapy. As mentioned above, the IPG 100 (or ETS 170) includes control circuitry 102 into which an ECAP algorithm 124a can be programmed. As also noted above, the ECAP algorithm can alternatively operate with the assistance of external devices, as shown in FIG. 10, which shows an external programming device (such as the clinician programmer 90 or external controller 50) in wireless communication with the IPG 100 (or ETS 170). In this example, an ECAP algorithm 124b is included in the external device, which can receive information from the IPG 100 (or ETS 170) regarding the ECAPs it measures, process the ECAP, and send a stimulation program (or adjustment) to the IPG. ECAP algorithm 124a again operates in the IPG 100 (or ETS 170), but in this example off-loads ECAP analysis and stimulation program adjustment to ECAP algorithm 124b in the external device. A system as shown in FIG. 10 is particularly useful when fitting the implant patient, i.e., when determining a stimulation program that would be useful in treating the patient's symptoms. One skilled in the art will understand that the ECAP algorithm 124a and 124b and/or any supporting user interface program will comprise instructions that can be stored on non-transitory machine-readable media, such as magnetic, optical, or solid-state memories. Such memories may be within the IPG or ETS itself (i.e., stored in association with control circuitry 102), within the external system, or readable by the external system (e.g., memory sticks or disks). Such memories may also include those within Internet or other network servers, such as an implantable medical device manufacturer's server or an app store server, which may be downloaded to the external system.

Figure 11:
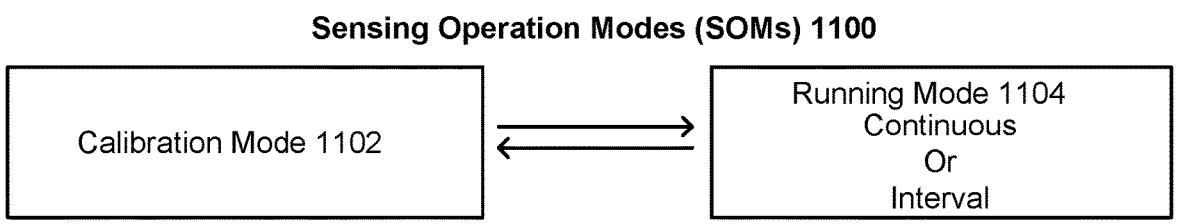
FIG. 11 shows operating modes of an ECAP algorithm.

Referring to FIG. 11, embodiments of the neuromodulation system and algorithm may comprise two sensing operating modes (SOMs) 1100—a calibration mode 1102 and a running mode 1104. The calibration mode 1102 will typically be executed during the fitting process with the aid of the clinician programmer 90 or an allowed "patient programmer" (given clinician permission) with specific programming features, though aspects of the calibration mode may be executed using the external controller 50. The running mode 1104 is generally executed by programmed circuitry within the IPG 100 (or ETS 170). Another difference is that the running mode 1104, can operate in real time or at pre-programmed intervals where the stimulation parameters are adjusted in real-time or at the pre-programmed intervals based on the running mode of the ECAP algorithm 124a.

Figure 12:
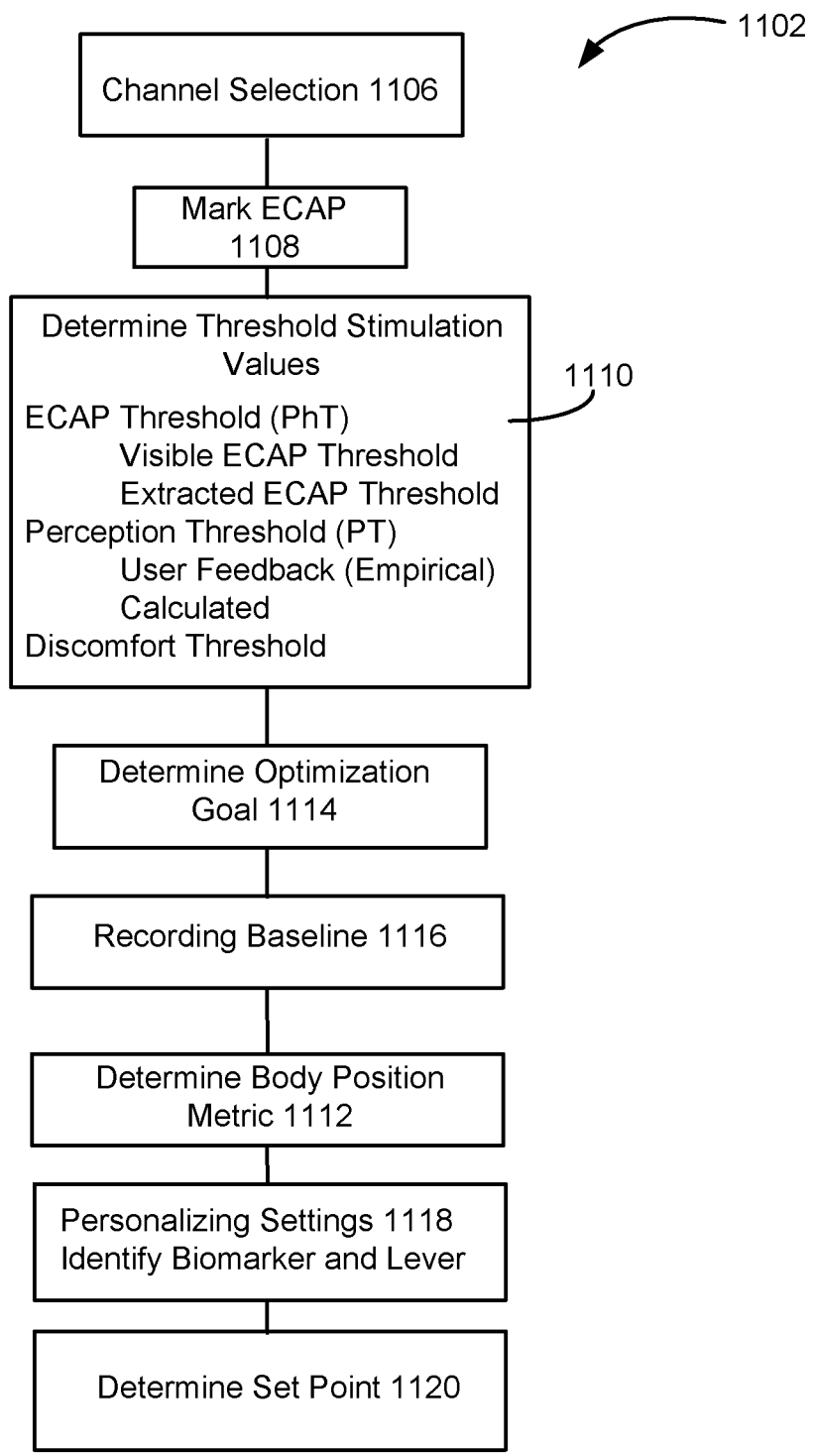
FIG. 12 shows aspects of an ECAP algorithm.

FIG. 12 illustrates the steps of an embodiment of the calibration mode 1102. An example of a system for interacting with the IPG 100 is described in "Precision Spectra™ System Programming Manual," Boston Scientific Corp., 90834018-18 Rev A (2016). The calibration mode may execute according to one of three modalities—(1) manual, according to which a user conducts all available tasks/steps; (2) semi-automatic, according to which a user conducts some tasks and selects other tasks to be conducted automatically; and (3) automatic, according to which the user selects all tasks to be conducted automatically. The user, typically a clinician, is presented with a user interface, such as a graphical user interface (GUI), which is configured to present the user with a representation of the electrical signals sensed at the various available implanted electrodes (channels), with buttons that allow the user to manually change the stimulation intensity or other stimulation parameter in the IPG 100, to determine specific threshold, such as perception threshold, ECAP threshold, discomfort threshold, or other threshold at a specific patient body posture or body activity. It should be noted, that although a clinician typically performs the calibration mode 1102 during the fitting procedure using the clinician programmer 90, the patient may also perform aspects of the calibration mode using the external controller 50 or a software application in smart device. In other words, the patient may periodically recalibrate certain aspects of their therapy. For example, the patient may find that their perception of the stimulation has changed and the patient can now perceive the stimulation at a particular body position. This may be because the position of the implanted leads shift with respect to their anatomical structures or because the patient's perception may change over time. The patient may recalibrate aspects of their therapy in such cases at any time and for any specified body position or body activity.

During the channel selection task 1106, the user may be presented with a representation of the available ECAP sensing channels (i.e., sensing electrodes). The user may have an idea of which ECAP sensing channel(s) should be selected based on the location of the leads within the patient's anatomy, which structures are to be stimulated, and a variety of other therapy-related variables. Stimulation can be delivered at preset settings with an initial, minimal amplitude. The amplitude is progressively increased until the user can detect ECAPS at one or more of the available channels. The user may select at least one sensing channel where the ECAP signal is visualized to the user's satisfaction.

Even in the absent of stimulation, the sensing electrodes will record the electrical noise floor signal produced by a combination of factors, including neural fibers and elements of the spinal cord and related structures that produce local field potentials and are not electrically silent, as well as movement artifacts from cardiac muscle, respiration, and internal and external body movements. When stimulation intensity is below perception threshold or at very small amplitudes, it may not be possible to observe a visual ECAP response that generally has to meet a SNR (Signal-To-Noise-Ratio) greater than 1 db (decibel) for the ECAP to be visible. Thus, for stimulation pulses of very small intensities sometimes between 100 uA and 800 uA, very low amplitude ECAPs may be buried under the background floor or noise floor. Signal processing extraction techniques may be used to extract ECAP responses.

Figure 13:
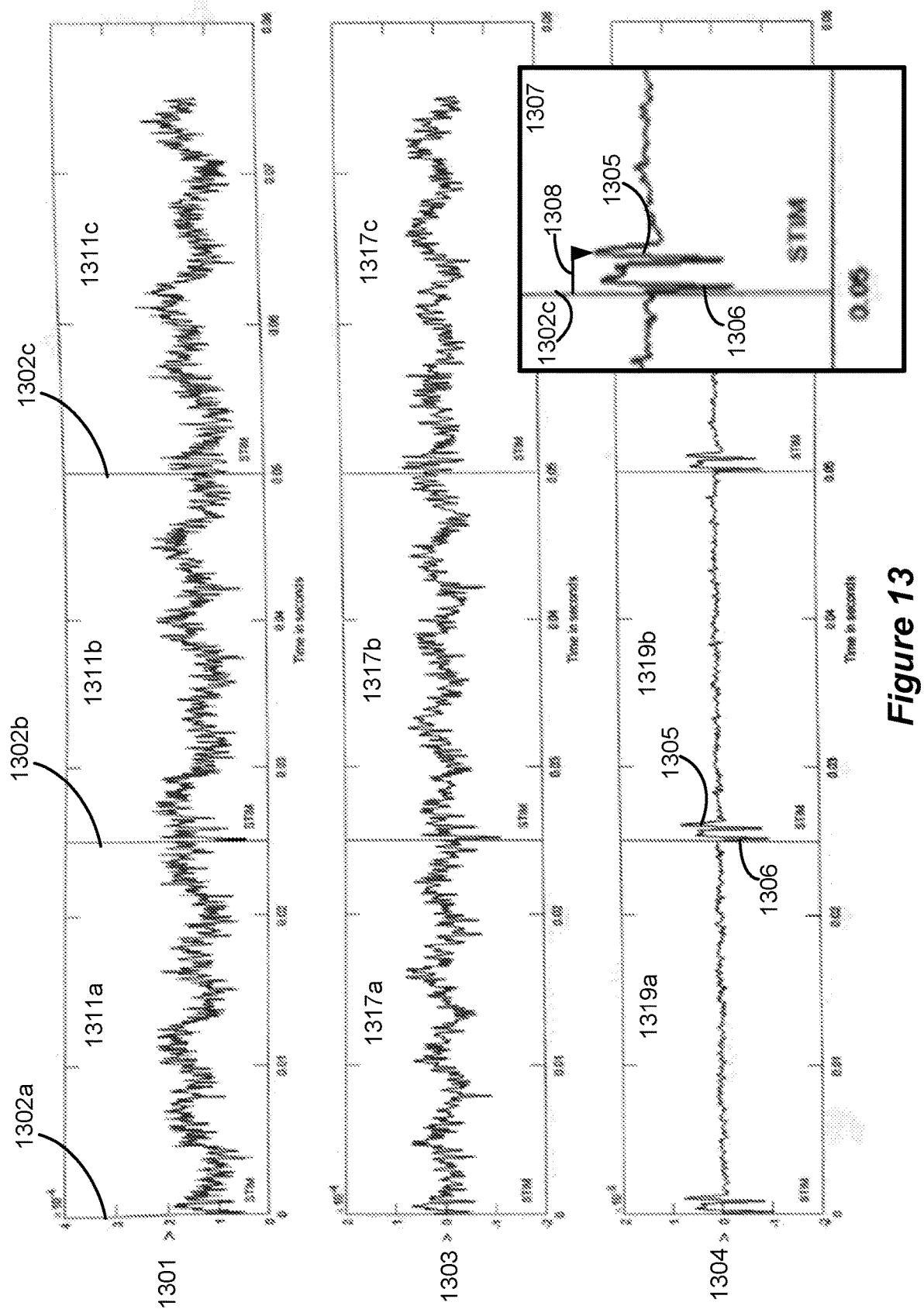
FIG. 13 shows an example of an ECAP extraction technique.

FIG. 13 illustrates an example of an ECAP extraction technique from data in an awake pig implanted with SCS leads. The top trace 1301 shows the electrical signal observed at a sense electrode (channel) when neural tissue is stimulated using 80 microsecond pulse-width and a stimulation frequency of 40 Hz. The vertical lines 1302a, 1302b, and 1302c indicate the time at which the stimulation pulses are delivered. The segments between the stimulating pulses, denoted as 1311a, 1311b, and 1311c, are referred to herein as "windows." As shown in trace 1301, electrical activity is present but is not visibly correlated to the timing of the pulses 1302a, 1302b, and 1302c.

The middle trace 1303 shows the electrical signal from 1301 at the same channel under the same conditions, but with a band pass filter applied. The trace 1303 comprises windows 1317a, 1317b, and 1317c. The bandwidth of ECAP signals typically includes frequencies of about 200 Hz to about 3 KHz. Thus, band pass filtering can be used accordingly to isolate electrical signals of those frequencies. Of course, the bandpass can be adjusted as needed. As seen in the middle trace 1303, the application of bandpass filtering decreases the noise of the trace, but still, no electrical activity visibly correlated to the pulse applications is observed.

Trace 1304 shows the signal averaged output derived from averaging 32 "windows" of the bandpass filtered signal. In other words, the signal contained within window 1319$a$ is an average of windows 1317$a$, 1317$b$, 1317$c$ . . . up to 32 windows. The number of windows used to compute the average may be selectable by the user. Noise cancels upon appropriate signal averaging and sharp, pulse-correlated ECAP responses 1305 are apparent. Artifacts 1306 deriving from the stimulation electric field are also visible. Inset 1307 shows a magnified view of an ECAP signal 1305 and an artifact signal 1306 resulting from averaging the previous 32 periods of the stimulation signal. Using the delay 1308 between the pulse 1302$c$ and the ECAP signal 1305 and the distance of the sensing electrode to the stimulating contact, it is possible to estimate the conduction velocity (CV) of the recruited neural structure. CV can also be computed using the relative approach where the ECAP delays from different sensing contacts are subtracted as well as the distance between these contacts to estimate CV as the distance divided by the delay difference. The ECAP extraction techniques illustrated in FIG. 13 can be used to detect ECAP signals evoked at low stimulation intensity. For example, without ECAP extraction, ECAP signals may not be visible at stimulation intensities below 800 microamps with pulse width of 80 microseconds, but baseline extraction may push the detection limits down to 300 microamps.

Once ECAP is detected on a selected channel, with or without the use of ECAP extraction processing, the user can mark 1108 the ECAP signal (FIG. 12), for example, by clicking on the ECAP. The marked ECAPs can be used to automatically or semi-automatically determine threshold values for different parameter settings combination and at different postures or body activity as explained below. Once an ECAP is stored for a selected channel, the ECAP visual threshold can be automatically determined by the system, and also the extracted ECAP threshold. Other thresholds (such as perception, discomfort, or others) can also automatically be determined, by establishing the relation between those other thresholds and the ECAP threshold during the calibration mode. For example, from the calibration mode, the perception threshold and the ECAP threshold (visual ECAP threshold or extracted ECAP threshold) are determined for specific stimulation settings and/or posture, therefore, the system can determine their relation and measure the ECAP threshold for different settings and/or posture and assess the perception threshold from the measured ECAP threshold.

According to some embodiments, the treatment algorithm uses ECAP metrics determined at two (or more) threshold neural stimulation intensities. Examples of threshold intensities may include (1) the extracted ECAP threshold is an extracted neural response threshold, which corresponds to the minimum stimulation at which an ECAP can be detected after signal processing techniques; (2) the visual ECAP threshold, which corresponds to the minimum stimulation at which an ECAP is visible (generally at a SNR of 1 db) (3) the perception threshold (PT), which corresponds to the minimum stimulation perceptible by the patient; (4) the discomfort threshold, which corresponds to the minimum stimulation intensity that causes discomfort for the patient and the (5) motor threshold, which corresponds at the minimum stimulation intensity that produces muscle activation by recruitment of motor fibers.

The extracted ECAP threshold is explained first. The extracted ECAP threshold is also referred to as the extracted physiological threshold (PhT) since it is the minimum stimulation that results in an extracted detectable evoked neural response. According to some embodiments extracted of ECAPs may have a magnitude about 10% of the raw sensed signal noise floor. The visual ECAP threshold is explained next. The visual ECAP threshold is the minimum stimulation intensity that results in a visible evoke physiological response. Generally, a SNR greater than 1 db is enough to allow visualization of the ECAP. According to some embodiments, the PhT may be taken as the minimum stimulation amplitude that results in a visible ECAP signal without ECAP extraction processing. Such a PhT is referred to herein as a visible ECAP threshold. According to some embodiments, ECAP extraction processing, as described above, may be used to lower the detection limits so that the PhT may be detected at a lower stimulation intensity. Such a PhT is referred to herein as an extracted ECAP threshold.

Another relevant threshold stimulation value is the perception threshold (PT), which is the minimum stimulation intensity at which the patient perceives the stimulation, typically as paresthesia. The PT intensity may of course be determined empirically based on patient feedback by gradually increasing the stimulation intensity until the patient reports a paresthesia sensation. Alternatively, PT may be estimated based on the ECAP threshold PhT, as:

$$PT = C \times PhT$$

where C is a programmable constant. In some cases, C is about 2, but it may generally be any number typically greater than 1, for example, 1.5, 2, 2.5, 3, etc. C may vary by patient, lead and contact location, stimulation parameters, etc. The value of C may be determined during the original calibration session and may be adjusted throughout therapy. The value of C may also vary with the posture or body activity and can be calibrated for different postures to determine $C_{min}$ (minimum C depending on posture or body activity) and $C_{max}$ (maximum C depending on posture or body activity). Referring to FIG. 12, the calibration mode 1102 includes a task for determining or entering a value for the perception threshold PT. In sum, the perception threshold PT is a second set of stimulation parameters where the patient perceives the stimulation, or that is calculated to evoke the patient's perception of the stimulation.

The calibration mode 1102 uses an optimization goal 1114 based on the threshold stimulation parameters described above to direct therapy that is optimized to provide relief to the patient. The user may input the optimization goal into the calibration algorithm or the optimization goal may be provided as a default value by the calibration algorithm. An example of an optimization goal 1114 may be to adjust stimulation values to maintain the ECAP signal or extracted metric from ECAPs at 50% between the extracted ECAP threshold (PhT) and the perception threshold (PT) values, or at any other preset percentage value desired. An initial optimization goal may be used during the calibration SOM 1102 and may be adjusted later during the running mode, as therapy progresses.

The calibration mode 1102 performs baseline recording of sensed spinal cord signals and conducts the extraction of ECAP signals from the noise floor while initial stimulation settings are delivered. The calibration mode may determine one or more metrics 1112 derived from the extracted ECAP signals for different postures and different body movement activity. Then, for the different postures the calibration mode 1102 progressively varies one stimulation parameter such as intensity, pulse width, frequency, cycling, pulse shape, stimulating electrode, or other, and it stores the extracted ECAPs and their metrics for the different postures. The ECAPs metrics are related to the stimulation parameter varied at each specific position or body activity. The calibration mode 1102 derives the relation between the stimulation parameter and the ECAP metric for each posture or body activity to determine appropriate set points as a function of body position. This variation in the stimulation parameter or adjustments to the initial stimulation parameters elicit changes in the sensed ECAP measurements to determine personalized settings 1118 for the particular patient. During the process of personalizing settings 1118, the calibration mode 1102 determines (1) which ECAP metrics are most sensitive to postural changes, body movement activity, changes in the stimulation parameters, and (2) which stimulation parameters and body positions elicit the greatest changes in the ECAP metrics. In other words, the personalizing settings process 1118 determines the most effective biomarkers (ECAP measurements) to track and the most influential body positions and the most potent "levers" (stimulation parameters) to adjust to maintain optimum therapy.

Having identified the metric(s) M to be used as effective biomarkers and the stimulation parameter(s) that most impact the biomarker, for the key postures and body movements the calibration mode 1102 may determine a set point or range of set points for the metric 1120 based on the optimization goal and the metric(s) M measured during calibration for the different postures. In one embodiment of the optimization goal can be to preserve the VOA (Volume of Activation) within an optimal range determined during the calibration and that can always be readjusted based on the running mode measurement of the feature metric. According to some embodiments, the set point S.P. or range of set points for the metric is a function of the stimulation parameter varied and also a function of the distances to the spinal cord of the stimulating electrode(s) and the sensing electrode(s), which will determine the volume of neural activation. Note that these distances may change with body movement or activity, and this is the rationale for calibrating for different positions and body activity. For example, set points may be defined as a function of body positions p, as follows:

$$S.P.(p) = K \times (M_{PT}(p) - M_{PhT}(p)) + M_{PhT}(p)$$

where S.P. is the set point metric, p is scalar indicating key specific positions, extreme postures where the electrodes are closer and farther from the spinal cord can be enough to determine the set point range, $M_{PT}$ is the metric determined at the perception threshold for posture p, and $M_{PhT}$ is the metric determined at extracted or visual ECAP threshold for posture p, and K is a constant related to the optimization goal. Note that the body postures can also be interpreted as distances from the stimulating and sensing electrodes to the spinal cord, and this distance can be different for the stimulating and sensing electrodes. For example, if the optimization goal is to maintain therapy at 50% between the ECAP threshold PhT and the perception threshold PT, then K may be set to 0.5. The initial set point programmed during the calibration can be an intermediate set point value between the most extreme body postures, which are the postures that produce the smallest and largest distance between the electrodes and the spinal cord. The set point is used during the running mode 1104 to maintain therapy as defined by the optimization goal, therefore as the metric extracted from the ECAP changes, the stimulation parameter selected as the controlled variable will be adjusted to maintain the same volume of activation or to maintain the same percentage between ECAP threshold PhT and perception threshold PT in the metric extracted from the ECAP measured. Note the look up table of set point values versus the stimulation parameter adjusted or controlled variable is determined during the calibration mode for the different postures or body activities.

The running mode 1104 is executed using the ECAP algorithm functions 124a configured with in the IPG 100 (or ETS 170), based on the set point and parameters determined during the calibration mode 1102. The running mode 1104 monitors the metric(s) M to determine when it changes above a minimum level and adjusts the chosen stimulation parameter(s) to maintain the metric(s) M according to the set point S.P.(p) or the set point range. In the running mode, the system does not know the p (body position), meaning it does not know the distance between the spinal cord and the electrodes. In one embodiment of the system, the running mode of the system can interpolate and estimate the level of posture change (change in distance between the spinal cord and the electrodes) by small changes in the appropriate direction to the stimulation parameter selected (controlled variable) that will produce small changes in the measured ECAP and will also produce small changes in the feature extracted from the ECAP to produce the extracted metric. After obtaining at least two of these pairs of values formed by the stimulation parameter and the extracted metric, a system of equations can be formed to solve for next optimal current to achieve the goal. The running mode 1104 may operate continuously or at defined intervals. Operating continuously, each stimulation invokes the running mode 1104. According to the continuous mode, the running mode 1104 includes a programmable sensing and analysis duration preceding and following each stimulus. The ECAP algorithm 124a detects the ECAP during the sensing and analysis window and adjusts the selected stimulation parameter(s) to maintain the set point S.P. According to the interval mode, the ECAP algorithm 124a assesses the ECAP metrics at defined time intervals. The intervals can be in the range of microseconds, milliseconds, seconds, minutes, hours, days, months, years, etc.

According to some embodiments, the ECAP algorithm is also programmed with the discomfort threshold determined during the calibration mode. The ECAP algorithm may adjust therapy if the measured ECAP metrics approach the value of the determined discomfort threshold.

According to some embodiments, the ECAP algorithm 124a may save a historic database of the ECAP metric measurements, for example, as trends or histograms. The saved ECAP measurements may be exported to an external device, for example, the external controller 50 or the clinician programmer 90, so that the historic database can be used to evaluate and/or modify therapy. According to one embodiment, the algorithm may associate patient feedback, for example, a patient comfort rating, with various stored data points.

As mentioned above, the patient may be provided with the ability to adjust or recalibrate aspects of the ECAP algorithm. For example, the patient's external controller 50 may include a recalibration mode, which may cause the ECAP algorithm to perform a subset of the steps of the calibration mode described above, including determination of perception threshold. According to one embodiment, the patient may be able to adjust the calibration set point, for example, by adjusting the constant K, in the set point equation above.

The signal processing extraction techniques used to extract ECAP responses described above have primarily been explained in the context of SCS. However, it should be appreciated that the extraction techniques and ECAP measurements can also be used for other neuromodulation modalities as well. For example, ECAP measurements can be used with peripheral nerve stimulation (PNS) modalities, particularly when targeting neural regions that have both afferent and efferent neural elements near one another. ECAP sensing and feedback can be used to selectively recruit only sensory or only motor fibers, as indicated. ECAPs can be used to limit spillover of stimulation to different fascicles within a nerve. In sacral nerve stimulation for overactive bladder (OAB), for example, electrodes are configured in electrical proximity or contact with sacral nerve fibers. ECAP feedback can be used to limit the stimulation of motor fibers and to help manage stimulation to target certain fibers and not others and to adjust stimulation settings automatically based on the ECAPs response for the selected stimulated fibers.

ECAP sensing and feedback, particularly including the signal processing extraction techniques described above, can also be used with vagus nerve stimulation (VNS), wherein the electrodes are configured in neural proximity or contact with vagus nerve fibers. For example, sensed ECAPs can be used as a biomarker for neural stimulation related to side effects of VNS, such as coughing or other voice disturbances, allowing stimulation to be titrated to optimize therapy while avoiding the side effect.

ECAP sensing and feedback, particularly including the signal processing extraction techniques described above, can also be used with deep brain stimulation (DBS), wherein the electrodes are configured in neural contact with neural tissue in the patient's brain. For example, sensed ECAPs can be used to determine field orientation/directionality. Moreover, ECAPs can be used to determine patient tremor level, bradykinesia, rigidity, body balance to automatically adjust therapy settings in a closed loop approach. A combined index can be computed that weights the different symptoms.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A medical device, comprising:
at least one implantable electrode lead comprising a plurality of electrodes each configured to be electrically coupled in contact with a patient's neural tissue; and
controller circuitry configured to:
issue a stimulation waveform, wherein the stimulation waveform is formed to provide pain relief below a perception threshold of the patient,
determine a neural response generated by the neural tissue in response to the stimulation waveform at at least one electrode of the plurality of electrodes;
determine at least one feature indicative of the neural response; and
based on the at least one feature, adjust the stimulation waveform to maintain the feature between a first threshold value corresponding to a minimum stimulation at which a neural response can be detected using signal averaging and a second threshold value corresponding to the perception threshold.

2. The medical device of claim 1, wherein the neural response comprises an Evoked Compound Action Potential (ECAP).

3. The medical device of claim 2, wherein the at least one feature comprises at least one of a shape of the ECAP or a size of the ECAP.

4. The medical device of claim 3, wherein the at least one feature comprises at least one of a height of a peak of the ECAP or a width of the ECAP.

5. The medical device of claim 3, wherein the at least one feature comprises at least one of an area of the ECAP or an ECAP peak.

6. The medical device of claim 3, wherein the at least one feature comprises at least one of a length of a portion of the ECAP.

7. The medical device of claim 2, wherein the at least one feature comprises at least one of a time defining a duration of a portion of the ECAP, or a time delay from neural stimulation to the ECAP.

8. The medical device of claim 1, wherein the controller circuitry determines the at least one feature of the neural response by comparing the at least one feature to at least one threshold or range.

9. The medical device of claim 8, wherein the at least one threshold or range comprises an extracted neural response threshold.

10. The medical device of claim 8, wherein the controller circuitry is configured to adjust the at least one threshold or range based on user input.

11. The medical device of claim 10, wherein the controller circuitry is configured to receive user input via telemetry from an external controller.

12. The medical device of claim 1, wherein the controller circuitry further comprises at least one amplifier configured to amplify the neural response at the at least one electrode.

13. The medical device of claim 12, wherein the controller circuitry further comprises at least one Analog-to-Digital converter configured to receive the output of the at least one amplifier and to digitize the amplified neural response.

14. The medical device of claim 1, wherein the controller circuitry is further configured to use filtering and averaging to extract a neural response from a noise floor.

15. A non-transitory computer-readable medium having instructions stored thereon to cause circuitry in a computing device to:
cause a medical device to issue a first stimulation waveform using one or more of a plurality of electrodes each configured to be electrically coupled in contact with a patient's tissue,
receive data from the medical device indicative of a first neural response generated by the neural tissue in response to the first stimulation waveform at at least one electrode of the plurality of electrodes,
cause the medical device to issue a second stimulation waveform using one or more of the plurality of electrodes,
receive data from the medical device indicative of a second neural response generated by the neural tissue in response to the second stimulation waveform at at least one electrode of the plurality of electrodes,
determine at least one feature of the first and second neural responses that changes based on differences between the first and second stimulation waveforms, and
determine at least one threshold or range of the at least one feature that correlates to a stimulation providing pain relief below a perception threshold of the patient.

16. The non-transitory computer-readable medium of claim 15, wherein the neural response comprises an Evoked Compound Action Potential (ECAP), and wherein the at least one feature comprises at least one of the shape of the ECAP, a size of the ECAP, a height of the ECAP, a width of the ECAP, an area of the ECAP or of an ECAP peak, a length of any portion of the ECAP, a duration of a portion of the ECAP, or a time delay of the ECAP from neural stimulation.

17. The non-transitory computer-readable medium of claim 15, wherein the at least one threshold or range is the perception threshold of the patient or the minimum stimulation at which an ECAP is detectable.

18. The non-transitory computer-readable medium of claim 15, further comprising instructions stored thereon to cause the circuitry in a computing device to display information related to the data indicative of a second neural response.

19. The non-transitory computer-readable medium of claim 15, further comprising instructions stored thereon to cause the circuitry in a computing device to transmit the threshold or range to the medical device.

20. A method of providing electrical stimulation to a patient's neural tissue using a medical device comprising at least one implantable electrode lead comprising a plurality of electrodes each configured to be electrically coupled in contact with the patient's neural tissue, the method comprising:
issuing a stimulation waveform, wherein the stimulation waveform is formed to provide pain relief below a perception threshold of the patient,
determining a neural response generated by the neural tissue in response to the stimulation waveform at at least one electrode of the plurality of electrodes;
determining at least one feature indicative of the neural response; and
based on the at least one feature, adjusting the stimulation waveform to maintain the feature between a first threshold value corresponding to a minimum stimulation at which a neural response can be detected using signal averaging and a second threshold value corresponding to the perception threshold.

* * * * *